United States Patent [19]
Knudson

[11] 3,936,936
[45] Feb. 10, 1976

[54] DENTAL CLINIC

[76] Inventor: William Lewis Knudson, 105 E. Skyline Drive, Brigham City, Utah 84302

[22] Filed: June 23, 1969

[21] Appl. No.: 835,454

[52] U.S. Cl. .......................... 32/1; 35/16
[51] Int. Cl.² ............................ A61C 19/00
[58] Field of Search ......... 312/209; 32/1, 22; 35/16; 128/1 R

[56] References Cited
OTHER PUBLICATIONS
Weberdental Catalogue, Office Planning Booklet, p. 15, Plan No. 8719B, May 1969.

*Primary Examiner*—Robert Peshock
*Attorney, Agent, or Firm*—B. Deon Criddle

[57] ABSTRACT

A dental clinic wherein two or more dentists can each efficiently handle two patients at one time. The dentist's operatory is divided by a cabinet wall containing operating equipment and independent patient access is provided from a separate reception area to both divided sections. A support area containing a clean-up section, laboratory and dark room is arranged to be easily accessible to each section of the operatory.

5 Claims, 2 Drawing Figures

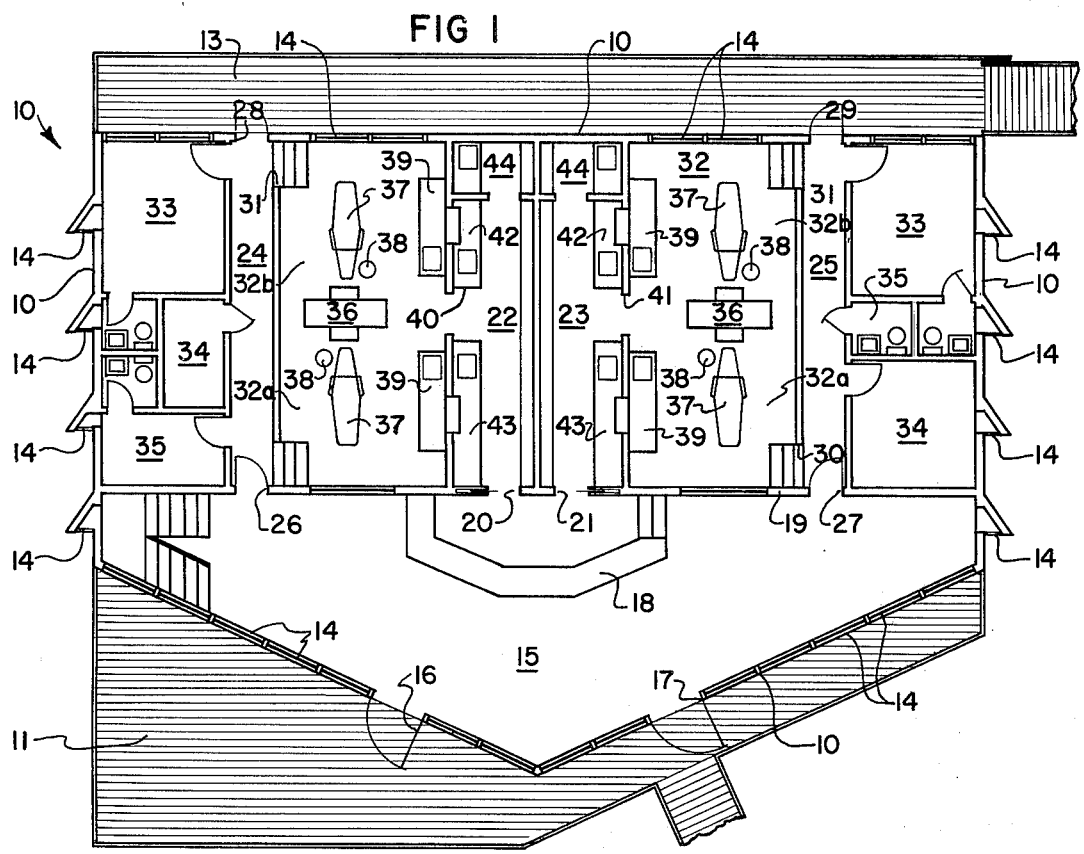
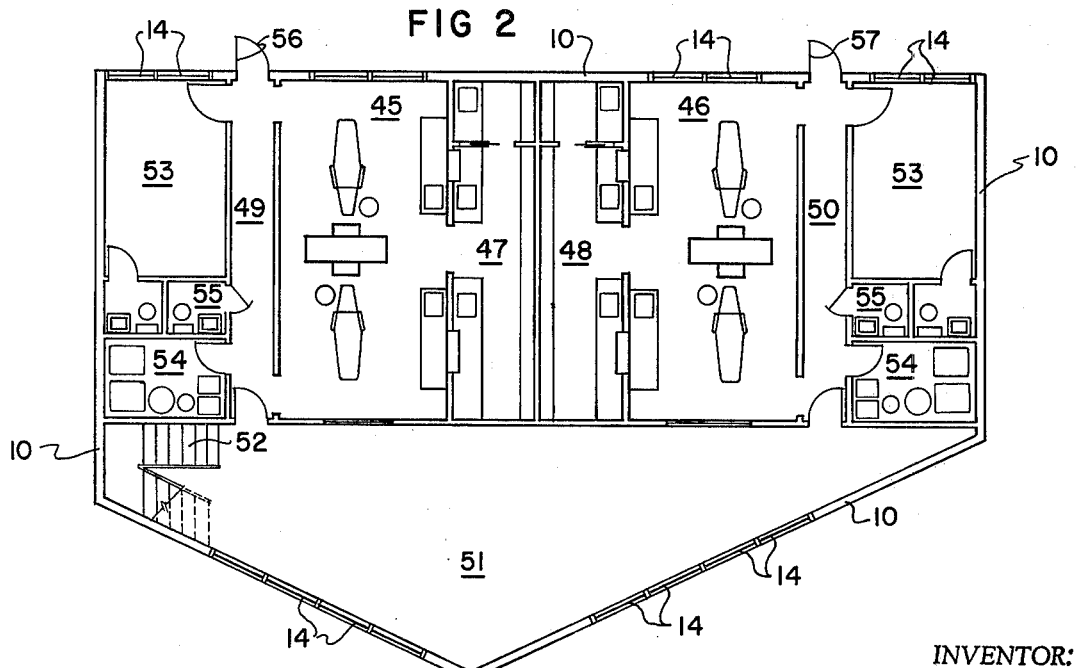

DENTAL CLINIC

BRIEF DESCRIPTION

In the practice of dentistry, it is imperative that if the dentist is to achieve maximum efficiency and productivity, he must be able to move from patient to patient with a minimum of wasted time and effort and a maximum conservation of movement. This means that as he finishes with one patient he must be able to immediately move to another without waiting for the time normally required to prepare the patient. Also, since some dental operations necessitate a wait during the operation, it is desirable to have another patient available on whom the dentist can operate during the delay. It is also important that patient apprehension be alleviated, that traffic patterns for both patients and dental personnel be open and free and that movement from patient to patient by the dental personnel be efficient and incorporate necessary activities that would otherwise require time delays and detours.

PRIOR ART

In the past, many dentists have attempted to achieve the desired efficiency and productivity by utilizing two or more independent rooms, each containing a full compliment of chair, drills, and other equipment and by then having a second patient prepared by an assistant while the dentist works on the first patient. This has been a great improvement on the prior practice of using a single chair and the completion of work on one patient before the next patient is prepared for examination and/or operation.

Nevertheless, these prior methods of handling patients, and the equipment and building arrangement used, have not been entirely satisfactory. They are generally wasteful of building area, equipment, or personnel and they frequently result in congestion as patents, dental assistants, clerical personnel and dentists move about within the dental clinic using common traffic patterns. Furthermore the formidable array of equipment and the constant activity of dental personnel present is both nerve wracking and destracting to the patient. Nervous apprehension is frequently increased too, as one patient who has been treated moves from the operatory through crowded corridors and a waiting room to exit the building.

Principal objects of this invention are to provide a dental clinic arranged such that maximum efficiency and productivity can be readily achieved.

Other objects are to provide a dental clinic wherein a single reception clerk can serve two or more dentists; a pair of patients can be prepared in complete privacy in patients chairs for concurrent treatment or examination; and each dentist has full mobility between the prepared patients and can make maximum use of common x-ray equipment, serving both patients chairs, while still having individual equipment such as drills and the like for each chair but located in a common wall cabinet, out of the view of the patients.

Still another object is to provide a dental clinic wherein optimum use is made of the space available and wherein the dental personnel and patients have free unobstructed movement throughout the clinic such that they do not adversely affect each other's movement and such that patients do not have to retrace their steps.

To accomplish these objects, I have provided, as principal features of my invention, a building having an entrance and reception area, a pair of corridors extending from opposite ends of the entrance and reception area, passageways at each end of each corridor opening to a dentist's operatory that is centrally divided by an equipment containing cabinet wall. Both sections of the operatory are adjacent to a support area containing a clean-up section, a laboratory and a dark room, and passage is provided between sections and between the support area and the operatory at the cabinet wall and at the side of the operatory opposite the passageways interconnecting the operatory room and a corridor.

Additional objects and features of the invention will become apparent from the following detailed description and drawing, disclosing what is presently contemplated as being the best form of the invention.

THE DRAWING

FIG. 1 is a floor plan of the main floor of the dental clinic building of the invention; and FIG. 2, is a similar view of a lower floor.

DETAILED DESCRIPTION

Referring now to the drawing:

In the illustrated preferred embodiment, the dental clinic of the invention includes a building having walls, shown generally at 10, a front deck 11, extending out from the front of the main floor 12, a rear deck 13, extending out from the rear of the main floor 12 and windows 14.

An entrance and reception room 15 extends fully across the front of the main floor 12, and doors 16 and 17 provide access to the entrance and reception room from the front deck 11.

A receptionists desk 18 is preferably provided centrally of the entrance and reception room and at the rear wall 19 of the room. The area behind the table than opens, through doorways 20 and 21 to support areas 22 and 23, respectively.

Corridors 24 and 25 extend respectively from doorways 26 and 27 at locations adjacent to opposite ends of the entrance and reception room through the building to rear doorways 28 and 29 opening onto rear deck 13. The rear doorways 28 and 29 thus serve as private entrances for dental personnel or for emergency patients who can be brought in without disturbing patients in the waiting room. While all patients can exit through the doors 28 and 29, it is particularly advantageous to have patients under stress exit this way, so that they do not upset waiting patients in the reception area.

Each corridor has two doorways 30 and 31, respectively, opening from one side of the corridor to one of the sections of an adjacent divided operatory 32 and, if desired, doorways opening from the other side of the corridor to an office 33, a storage area 34, and a rest room 35.

Each operatory 32 is divided by a wall cabinet 36 into sections 32a and 32b and each section contains a patients chair 37, facing away from the wall cabinet, a dental stool 38, for use by the dentist and sink containing cabinet 39.

Support area 22, opens through doorway 40 to one operatory 32 and support area 23, opens in similar fashion, through doorway 41 to the other operatory 32.

Each laboratory area includes sink containing cabinets 42 and 43 at opposite sides of the doorway to the adjacent operatory room and a dark room 44 at one end thereof in which x-ray film can be developed. Cabinets 42 contain sterilization units and provide the clean-up section of the support area and cabinets 43 provide the laboratory area where plasters, etc. are prepared.

The doorways 40 and 41 open centrally into the operatory so that either section of the operatory is mutually accessible to the laboratory, and yet the support area is not viewed by a patient in either patients chair. Thus activities in the support area do not distract the patient or add to his apprehension.

Since the wall cabinet 36, extends only partially across the operatory and centrally thereof the dentist and his assistants can move freely from one section of the operatory to the other and to the support area.

In practice, the dentist will leave a patient in one chair 37, move directly around the clean-up area side of the cabinet wall 36, to the sink in the cabinet of the other section of the operatory, scrub up, in the view of the patient in the other chair and move to that patient to begin or continue work. Simultaneously, the dentists chair assistant will leave the first patients chair, go to the sink of the cabinet in the first patients section of the operatory, scrub up and then move around the other side of the cabinet wall to the patient in the other chair. Thus, both the dentist and his assistant can simultaneously scrub up, they do not have to travel in the same traffic patterns and maximum time and motion efficiency is obtained.

Since the chairs 37 are arranged back to back, with the cabinet wall unit 36 between them, the travel distance of the dentist and his assistant is kept to a minimum.

While a single operatory arranged as herein disclosed, together with the support area, reception room and corridor is highly efficient for use by a single dentist, the use of a pair of operatories off of a single reception room adds to the efficiency of personnel since a single clerk receptionist and/or roving assistant can then readily handle patients for two dentists. The efficiency is even further increased if another floor, containing similarly arranged operatories and support areas and accessible from a common reception area is used. Thus, as shown in FIG. 2, additional divided operatories 45 and 46 are arranged to have support areas 47 and 48, corresponding to the operatory areas 22 and 23, previously described, connected thereto.

Corridors 49 and 50 lead from a waiting area 51 that, through stairs 52 forms a continuation of the entrance and reception area and, as with corridors 24 and 25, doorways open from each corridor to each section of its adjacent operatory and to an office 53, a store room 54 (which may contain heating and air conditioning equipment) and a rest room 55. The cabinet wall unit, chairs and cabinets of the lower floor operatories are arranged the same as those on the upper floor operatories.

With this arrangement, a single clerk-receptionist located in the entrance and reception area can readily handle incoming patients for as many as four dentists, and each patient can move to the proper section of his assigned operatory without disturbing any other patient and without crossing the normal working time traffic pattern of the dental personnel.

A roving assistant can easily prepare one patient at one side of the wall cabinet while the dentist and his chair assistant are working on a patient at the opposite side. The dentist and the chair assistant can then move from patient to patient as allowed by the dental procedures taking place and they can quickly move to a next prepared patient as soon as they have completed work on a first patient, in the manner previously described.

The patients can move easily from the entrance and reception area, through the proper corridor to either section of the operatory of the assigned dentist. After the dental procedure the patient can move easily out of the building through either front doorways 16 or 17 or rear doorways 28 and 29 or 56 and 57 on the lower floor.

Each dentist and his assistants normally operate in a zone comprising a support area and the operatory room when patients are present, and utilize the office and store rooms across the adjacent corridor only before or after patients are present. There is never any need for the dentist to pass through the entrance or reception area during his business day, a single clerk-receptionist area may serve a multiple number of dentists, and patient traffic is unobstructed and does not cross the traffic pattern of the dental personnel.

The wall cabinet 36 is equipped with such items of equipment as an x-ray unit with an extendible or movable head at each side of the wall cabinet such that the x-ray unit can be commonly used on both sides of the cabinet. Since it is necessary for the dental personnel to be shielded behind the cabinet wall as x-ray pictures are taken, it is not possible to take simultaneous x-rays on both sides and a single unit will suffice. A complete set of drills and other equipment is preferably provided at each side of the cabinet wall so that no delays will be encountered in patient treatment.

While a preferred embodiment of the invention has been herein disclosed, it should be obvious that variations are possible and that the storage rooms and offices, for example, can be rearranged without affecting the essential plan of the dental clinic.

I claim:
1. A dental clinic comprising
   a building having an entrance and reception area;
   at least one corridor extending from the entrance and reception area;
   an operatory adjacent to each said corridor;
   a wall cabinet containing dentist's equipment extensible out from each side thereof, extending partially across each operatory centrally thereof and dividing the operatory into sections;
   a doorway from each said corridor opening into each section of the operatory; and
   a patient's chair in each section arranged such that a patient sitting therein is facing away from the wall cabinet.
2. A dental clinic as in claim 1, further including
   a support area adjacent to each operatory;
   a doorway interconnecting the adjacent support area and the operatory centrally of the operatory and at a location behind the patients chairs.
3. A dental clinic as in claim 1, wherein
   a plurality of corridors are provided, each extending from the entrance and reception area; and further including
   a plurality of operatories, each having a wall cabinet therein to divide the operatory into sections and an entrance way into each section from one of said corridors.
4. A dental clinic as in claim 2, further including
   a doorway interconnecting the laboratory area and the entrance and reception area.

5. A dental clinic as in claim 4, wherein a pair of sinks are positioned within each operatory, with one sink at each side of the doorway interconnecting the support area and the operatory.

* * * * *